United States Patent
Hasse et al.

(10) Patent No.: US 8,684,987 B2
(45) Date of Patent: Apr. 1, 2014

(54) SELF-ORIENTING TAMPON HAVING IMPROVED ASPECT RATIO

(75) Inventors: Margaret Henderson Hasse, Wyoming, OH (US); Diana Lynn Gann, Lebanon, OH (US); Thomas Ward Osborn, III, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 729 days.

(21) Appl. No.: 11/703,946

(22) Filed: Feb. 8, 2007

(65) Prior Publication Data

US 2008/0195028 A1  Aug. 14, 2008

(51) Int. Cl.
*A61F 13/20* (2006.01)

(52) U.S. Cl.
USPC .................. 604/385.17; 604/904

(58) Field of Classification Search
USPC .......................... 604/385.17, 904
See application file for complete search history.

(56) References Cited

U.S. PATENT DOCUMENTS

| | | | |
|---|---|---|---|
| 3,068,867 A * | 12/1962 | Bletzinger et al. | 604/15 |
| 3,306,295 A * | 2/1967 | Penksa | 604/385.18 |
| 3,712,305 A | 1/1973 | Wennerblom et al. | |
| 3,794,029 A | 2/1974 | Dulle | |
| 3,971,378 A | 7/1976 | Krantz | |
| 4,266,546 A * | 5/1981 | Roland et al. | 604/365 |
| 5,383,891 A | 1/1995 | Walker | |
| 5,772,645 A * | 6/1998 | Zadini et al. | 604/358 |
| 6,177,608 B1 * | 1/2001 | Weinstrauch | 604/380 |
| 6,358,235 B1 | 3/2002 | Osborn, III et al. | |
| 6,554,814 B1 | 4/2003 | Agyapong et al. | |
| 6,635,800 B2 | 10/2003 | Jackson et al. | |
| 6,645,136 B1 * | 11/2003 | Zunker et al. | 600/29 |
| 6,682,513 B2 | 1/2004 | Agyapong et al. | |
| 6,719,743 B1 * | 4/2004 | Wada | 604/385.18 |
| 6,740,070 B2 | 5/2004 | Agyapong et al. | |
| 6,837,882 B2 | 1/2005 | Agyapong et al. | |
| 6,953,456 B2 | 10/2005 | Fuchs et al. | |
| 2004/0199137 A1 * | 10/2004 | Lamb | 604/385.18 |

FOREIGN PATENT DOCUMENTS

DE         299 09 321 U1     9/1999

OTHER PUBLICATIONS

PCT International Search Report dated Nov. 6, 2008.

* cited by examiner

*Primary Examiner* — Lynne Anderson
(74) *Attorney, Agent, or Firm* — Wednesday G. Shipp; Andrew J. Hagerty

(57) ABSTRACT

A tampon having an improved aspect ratio is provided. The tampon includes a self-sustaining, fluid-expanding, compressed absorbent pledget having one or more absorbent materials. The tampon has a width, a thickness, and a length. The width can be greater than the thickness and an aspect ratio of the width to the thickness can be from greater than about 1.4:1 to less than about 2.0:1. Also provided is a method of positioning a tampon within a vagina of a woman.

2 Claims, 2 Drawing Sheets

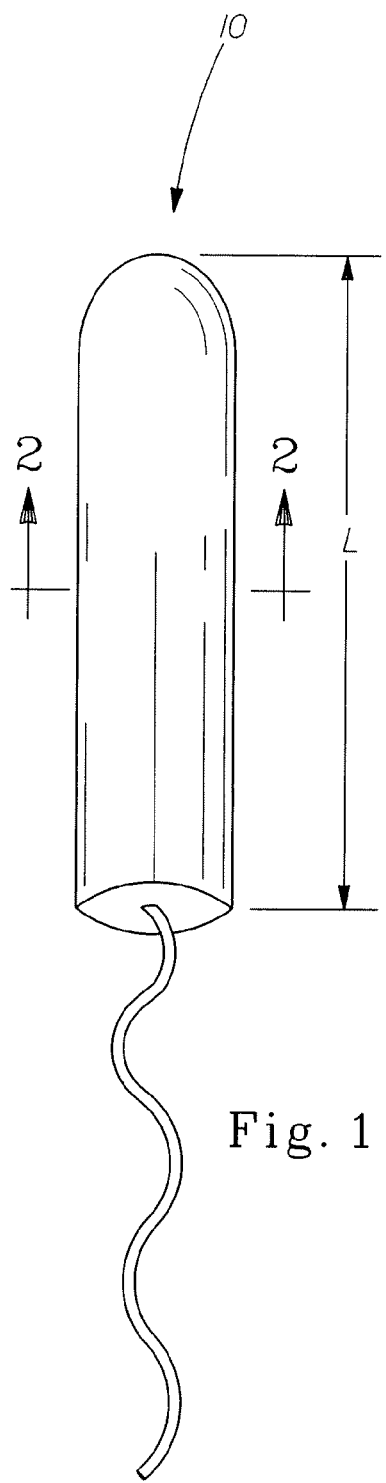
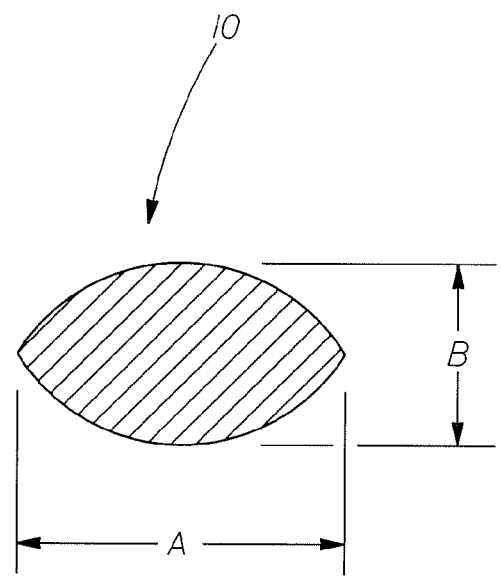
Fig. 1
Fig. 2

SELF-ORIENTING TAMPON HAVING IMPROVED ASPECT RATIO

FIELD OF THE INVENTION

The present invention relates generally to self-orienting tampons, more particularly to self-orienting tampons having improved aspect ratios.

BACKGROUND OF THE INVENTION

Feminine hygiene products, such as tampons and pessaries, are generally used by women within the vagina for feminine needs, such as, e.g., to absorb menstrual or other body exudates, for pelvic support, and/or for other feminine needs. Such feminine hygiene products can be inserted into the vagina digitally, such as, e.g., by using a finger, or can be inserted into the vagina by using an applicator.

It is a common misconception that the vagina is shaped like a cylindrical tube. In actuality, the vagina is a pocket that is irregular in shape with a length from the introitus to the cervix. When not distended by a foreign object, the vagina may resemble a pear shape in appearance when viewed from the coronal or front view of the female anatomy. From the sagittal or side view, the vagina is a long, thin muscular structure. Menstrual fluid typically enters the vagina through the cervix, which is generally located near the top of the vagina where the vagina is widest.

Currently available catamenial tampons are typically in the form of a cylinder prior to insertion in the vagina. Such tampons are generally formed from pledgets larger in size than the vaginal orifice. The pledgets are compressed to a smaller, generally cylindrical form with a circular cross-sectional shape in order to facilitate insertion into the vagina via the relatively narrow introitus. As fluid is absorbed from the vagina, these tampons are intended to re-expand toward their original pre-compressed size to eventually effectively cover the vaginal cavity against fluid leakage or bypass; however, such tampons can fail to re-expand sufficiently or fast enough to provide good coverage and thus can fail to provide sufficient leakage protection. As a result, menstrual fluid can bypass the tampon and leak outside the user's body.

Therefore, it would be desirable to provide a tampon with improved expansion generally focused in the width dimension, such as, e.g., to achieve maximum side to side coverage of the vagina. Because the ability of a tampon to expand widthwise can be limited when compressing a pledget into a circular cylindrical form, such as, e.g., the form of tampons generally commercially available today, it would also desirable to provide a tampon having an improved aspect ratio as compared to commercially available tampons. Furthermore, circular cylindrical tampons having improved expansion in the width dimension can be difficult to orient within the vagina such that the area of greatest expansion will correspond to the width of the vagina, because, for example, the symmetry of the compressed tampon shape conceals the proper orientation of the tampon from the user. This can result in the user inadvertently inserting the tampon such that the area of greatest expansion occurs perpendicular to the vagina instead of aligned with the width. As such, it would be desirable to provide a tampon with the ability to properly self-orient within the vagina of a user.

SUMMARY OF THE INVENTION

A tampon having an improved aspect ratio is provided. The tampon can comprise a compressed absorbent pledget formed of one or more absorbent materials. The tampon has a width, a thickness, and a length. The width can be greater than the thickness and an aspect ratio of the width to the thickness can be from greater than about 1.4:1 to less than about 2.0:1.

Also provided is a method of positioning a tampon within the vagina of a woman. The method can include providing a tampon having an aspect ratio and inserting the tampon into the vagina, wherein one or more intravaginal body pressures of the woman can position the tampon with the width of the tampon substantially aligned with the width of the vagina.

Further provided is a tampon applicator. The applicator can include a barrel and a plunger. The plunger can be telescopically and slidably mounted in the barrel. The barrel can have a tampon with an aspect ratio disposed therein. The tampon can include a self-sustaining, fluid-expanding compressed absorbent pledget comprising one or more absorbent materials. In addition, the tampon can have a width, a thickness, and a length, the width being greater than the thickness, and an aspect ratio of the width to the thickness can be from greater than about 1.4:1 to less than about 2.0:1. The barrel can be adapted to permit rotation of a tampon within the barrel relative to the barrel upon application of one or more intravaginal body pressures of a woman.

BRIEF DESCRIPTION OF THE DRAWINGS

FIG. 1 is a plan view of one embodiment of the present invention.

FIG. 2 is a cross-sectional view of the embodiment shown in FIG. 1.

DETAILED DESCRIPTION OF THE INVENTION

Figures 3, 4:
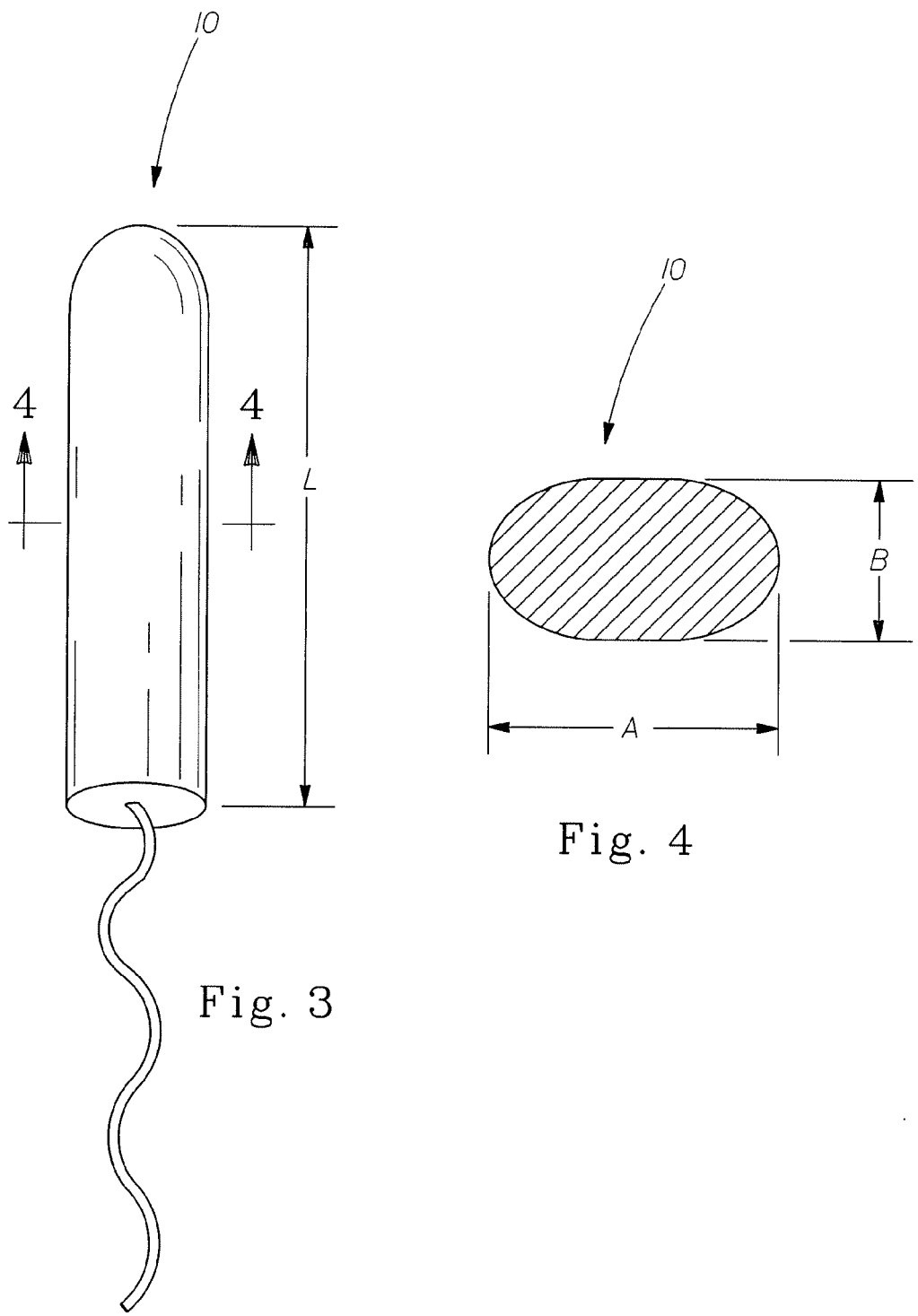
FIG. 3 is a plan view of one embodiment of the present invention.
FIG. 4 is a cross-sectional view of the embodiment shown in FIG. 3.

The present invention relates to tampons having an improved aspect ratio. Such tampons can self-orient within the user's body such that widthwise expansion generally occurs aligned with the width of the vagina. The tampons can comprise a pledget having a greater width than length that can be compressed to form a tampon with an improved aspect ratio. In certain embodiments, the tampon can have a substantially oval cross-section. The present invention further relates to a method of positioning at least a portion of a tampon between the cervix and the posterior wall of a vagina of a woman and a tampon applicator for positioning the tampon within a user's body.

As used herein, the term "tampon" refers to any type of absorbent structure that can be inserted into the vaginal canal or other body cavity, such as, e.g., for the absorption of fluid therefrom, to aid in wound healing, and/or for the delivery of materials, such as moisture or active materials such as medicaments. In general, the term "tampon" is used to refer to a finished tampon after the compression and/or shaping process. Tampons are generally constructed from an absorbent material that has been compressed in one or more of the width direction, the radial direction, and/or the axial direction to provide a tampon having a size and stability that allows insertion within the vagina or other body cavity. A tampon that has been so compressed is referred to herein as a "self-sustaining" form. That is, the degree of compression applied to the absorbent material of the tampon pledget is sufficient so that the resulting tampon will tend to retain its general shape and size in the absence of external forces. Once the tampon is inserted and begins to acquire fluid, the tampon can begin to expand and may lose its self-sustaining form. In certain embodiments, tampons constructed according to the present invention are fluid expanding. As used herein, the term "fluid-expanding" refers to a tampon that has been compressed into a self-sustaining form and that can expand or uncompress upon contact with fluid such as bodily fluids. Fluid-expanding tampons are contrasted to "mechanically expanding" tampons, which are tampons that use springs, or some other mechanical supplier of force, to expand.

As used herein, the term "pledget" refers to an absorbent material prior to the compression and/or shaping of the material into a tampon. Pledgets are sometimes referred to as tampon blanks or softwinds.

As used herein, the term "insertion end" refers to the portion of the tampon that is intended to enter the vaginal canal first when inserting the tampon.

As used herein, the term "withdrawal end" refers to the portion of the tampon opposite the insertion end is intended to exit the vaginal canal first when the tampon is removed from the vagina.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

As used herein, the term "applicator" refers to a device or implement that facilitates the insertion of a tampon into an external orifice of a mammal.

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

As used herein, the term "aspect ratio" refers to the ratio of the width of the compressed tampon to the thickness of the compressed tampon.

FIG. 1 is a perspective view of one embodiment of the invention. FIG. 1 shows a tampon 10 with an improved aspect ratio. In this embodiment, the tampon has a substantially oval cross-section and a length L. FIG. 2 is a cross-sectional view of FIG. 1, showing the tampon 10 has a width A and a thickness B. The tampon 10 has a cross-sectional shape similar to a football, such as, e.g., a cross-sectional shape in the form of a prolate spheroid. The aspect ratio of tampon 10 is represented as A:B. In certain embodiments, the length L can be measured from the insertion end of the tampon to the withdrawal end of the tampon, with the width A and the thickness B running perpendicular to the length L and to each other. Generally, the width A is larger than the thickness B.

FIG. 3 is a perspective view of one embodiment of the invention. FIG. 3 shows a tampon 10 with an improved aspect ratio. In this embodiment, the tampon has a substantially oval cross-section and a length L. FIG. 4 is a cross-sectional view of FIG. 3, showing the tampon 10 has a width A, and a thickness B. The tampon 10 has a cross-sectional shape similar to a racetrack. The aspect ratio of tampon 10 is represented as A:B.

In certain embodiments, the tampon can have an improved non-uniform expansion, such as, e.g., improved widthwise expansion. Tampons with improved widthwise expansion can have an expansion force in the width dimension greater than the expansion force in the thickness dimension and/or the length dimension. In certain embodiments, the expansion force in the thickness dimension can be about zero. In addition, or alternatively, the expansion force in the length dimension can be about zero.

The tampon can have an improved aspect ratio. The improved aspect ratio has been discovered to facilitate proper orientation of the tampon upon insertion into a user's vagina. In certain embodiments, the tampon can be compressed into a self-sustaining form and the tampon can self-orient within a user's vagina prior to the loss of the self-sustaining form.

While not desiring to be bound by any particular theory, tampons having an aspect ratio greater than about 1.4:1 can orient in the user's body during and/or shortly after insertion such that the width of the tampon is substantially aligned with the width of the vagina. In certain embodiments, the tampon can have an aspect ratio such that the tampon can properly orient in a user's body such that the width of the tampon is substantially aligned with the width of the vagina independent of tampon insertion.

The tampon can have any suitable aspect ratio, such as, e.g., an aspect ratio suitable for properly orienting in a user's body. For example, a typical commercially-available tampon that is formed with a substantially circular cross-section generally can have an aspect ratio of 1:1 to 1.2:1. Tampons with an improved aspect ratio, on the other hand, can have an aspect ratio greater than about 1.4:1, such as, for example, aspect ratios of about 1.5:1, about 1.6:1, about 1.7:1, 1.8:1, 1.9:1, or 2.0:1. In certain embodiments, a tampon having an improved aspect ratio can have an aspect ratio from greater than about 1.4:1 to less than about 2.0:1, such as, e.g., about 1.41:1 to about 1.99:1, such as, e.g., about 1.45:1 to about 1.95:1, such as, e.g., about 1.5:1 to about 1.9:1. In addition, or alternatively, a tampon having an improved aspect ratio can have an aspect ratio from greater, than about 1.4:1 to less than about 1.9:1, such as, e.g., about 1.41:1 to about 1.89:1, such as, e.g., about 1.45:1 to about 1.85:1, such as, e.g., about 1.5:1 to about 1.8:1. Generally, the tampon can have an aspect ratio suitable to facilitate the tampon orienting in a user's body such that the width of the tampon is substantially aligned with the width of the vagina in more than about 10% of insertions, such as, e.g., more than about 20%, more than about 30%, more than about 40%, more than about 50%, more than about 60%, more than about 70%, more than about 80%, more than about 90%, or about 100% of insertions.

The tampon can have an improved aspect ratio along any suitable portion of the tampon length. In certain embodiments, the tampon can have an improved aspect ratio along at least about 20% of the length, such as, e.g., at least about 25%, at least about 30%, at least about 35%, at least about 40%, at least about 45%, at least about 50%, at least about 55%, at least about 60%, at least about 65%, at least about 70%, at least about 75%, and/or along substantially the entire length. In certain embodiments, the tampon can have one or more improved aspect ratios along the length.

In certain embodiments, the width of the tampon can be measured at the widest point along the length of the tampon. In addition, the thickness of the tampon can be measured at the thickest point along the length of the tampon. In certain embodiments, the tampon can have substantially the same width and/or thickness along substantially all of the length of the tampon. In other embodiments, the tampon can have a varying width and/or thickness along substantially all of the length of the tampon, such as, e.g., a tampon having a larger width and/or thickness at the widthdrawal end and tapering to a smaller width and/or thickness at the insertion end.

The tampon's total length can be measured from the insertion end to the withdrawal end along the length. In certain embodiments, a typical tampon for human use can be generally about 10 to about 16 millimeters wide and about 30 to about 60 millimeters long, often depending on absorbency, but can be any suitable width and length. For other mammals, typical tampon dimensions can vary based on differences in their particular vaginal canal geometry. In certain embodiments, the tampon can have a thickness less than about 10 millimeters, less than about 9 millimeters, less than about 8 millimeters, or any other suitable thickness.

The tampon and any component thereof can comprise a single material or a combination of materials. In certain embodiments, the tampon comprises a compressed absorbent mass, such as, e.g., a compressed absorbent mass formed from compressing a pledget that consists essentially of one or more absorbent materials. The materials can be formed into a fabric, web, batt, or other construction suitable for use in a tampon pledget by any suitable process such as, for example, airlaying, carding, wetlaying, hydroentangling, or other techniques.

The pledget can be constructed from one or more absorbent materials suitable for use in an absorbent article. Such materials include, for example, rayon (such as GALAXY rayon (a tri-lobed rayon) or DANUFIL rayon (a round rayon), both available from Kelheim Fibres GmbH of Kelheim, Germany), cotton, folded tissues, woven materials, nonwoven webs, synthetic and/or natural fibers or sheeting, comminuted wood pulp, which is generally referred to as airfelt, or combinations of these materials. Examples of other suitable materials include: creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Additionally, superabsorbent materials, such as superabsorbent polymers or absorbent gelling materials can be incorporated into the tampon.

In certain embodiments, the pledget can include one or more absorbent materials, such as, e.g., rayon and/or cotton, that are randomly distributed throughout the pledget, such as, e.g., in a substantially uniform manner throughout the pledget. For example, the one or more absorbent materials can be mixed together and can be formed into a fibrous mat, or other construction by a suitable process such as, for example, airlaying, carding, wetlaying, hydroentangling, or other techniques, such that the one or more absorbent materials are distributed throughout the pledget. In other embodiments, the pledget can be a laminar structure comprised of integral or discrete layers. For example, the pledget can comprise outer layers and at least one intermediate layer positioned between the outer layers. The layers can be the same or different materials. Alternatively, or in addition, the pledget can comprise a folded structure, a rolled structure, a "petal" structure or any other suitable structure. In certain embodiments, the pledget can contain varying amounts of absorbent material across the length and/or width.

The pledget can be any suitable shape, size, material, or construction prior to compression and/or shaping. For example, the pledget can include a rolled, tubed, or flat construction of an absorbent that can be a circle, an oval, a semi-circle, a rectangle, a trapezoid, a triangle, a chevron shape, an H shape, a bow-tie shape, or any other suitable shape, such as, e.g., shapes described in, for example, U.S. Pat. Nos. 3,738,364; 5,911,712; 6,554,814; 6,682,513; 6,740,070; 6,837,882; 6,887,266; and 6,953,456. In certain embodiments, the pledget can comprise a length and a width, wherein the width is longer than the length.

The pledget can be compressed in the width direction, the radial direction, the axial direction, or in any combination of these directions to form a tampon. In certain embodiments, the greatest compression of the pledget can occur in the width direction. Insertion end formation of the finished tampon can be achieved by subsequent and less substantial compression in the axial direction.

The tampon can be made by any suitable method, such as, e.g., methods known in the art. Suitable methods include, for example, methods that impart heat and/or pressure to the tampon pledget. Such heat and/or pressure cause the fibers to "set" and achieve the compressed form until released by fluid absorption.

The tampon can be compressed to have a width and a thickness, such as, e.g., a generally self-sustaining width and thickness. In certain embodiments, the width of the tampon can be greater than the thickness to provide an improved aspect ratio, such as, e.g., described herein. The tampon can be formed to have any suitable cross-sectional shape, such as, e.g., an oval cross-sectional shape, a rectangular cross-sectional shape, a triangular cross-sectional shape, a trapezoidal cross-sectional shape, a semi-circular cross-sectional shape, or other suitable shapes. The cross-sectional shape can be the same size along the length of the tampon or, alternatively, can vary in size and/or proportion along the length. For example, the tampon can have a cross-sectional shape of a first size, such as, e.g., an oval cross-sectional shape of a first size, near the withdrawal end, and the same cross-sectional shape of a second size, such as, an oval cross-sectional shape of a second size, such as, e.g., a smaller size, near the insertion end of the tampon. In certain embodiments, the tampon can have more than one cross-sectional shape along the length of the tampon, such as, e.g., a cross-sectional shape of a first size near the insertion end of the tampon, a cross-sectional shape of a second side near the center of the tampon, and a cross-sectional shape of a third size near the withdrawal end. The cross-sectional shapes can be the same or different cross-sectional shape.

The tampon can have a fan-folded construction, such as, for example, wherein the pledget has a series of longitudinal, generally parallel folds that can be provided prior to and/or as a result of the compression of the pledget into the tampon. The tampon can have any suitable number of folds, such as, e.g., from about 1 to about 25, from about 3 to about 20, from about 4 to about 18, from about 6 to about 17, and/or from about 9 to about 15. The folds can be of any suitable size and/or uniformity.

The tampon can optionally include a withdrawal cord, a secondary absorbent member, and/or a liquid permeable overwrap material. Withdrawal cords useful in the present invention can be made of any suitable material known in the prior art, such as, e.g., cotton and rayon. The tampon of the present invention can also benefit from a secondary absorbent member, such as, e.g., secondary absorbent members described in U.S. Pat. No. 6,258,075. The tampon can also or alternatively comprise an overwrap. The overwrap can be any suitable material, such as, for example, rayon, cotton, bicomponent fibers, polyethylene, polypropylene, other suitable natural or synthetic fibers known in the art, and/or mixtures thereof. In certain embodiments, the tampon can comprise an overwrap material that substantially encloses the compressed tampon.

In certain embodiments, the tampon can be inserted digitally. When the tampons are intended to be digitally inserted, it can be desirable to provide a finger indent at the withdrawal end of the tampon to aid in insertion, such as, e.g., finger indents described in U.S. Pat. No. 6,283,952, and/or to aid in orientation. In certain embodiments, the digital tampon can comprise an overwrap material that extends from the withdrawal end and forms a finger cover. The digital tampon can also or alternatively comprise a covering material that extends from the withdrawal end and forms an absorbent skirt.

Alternatively, the tampon can be inserted using an applicator. Any suitable applicator can be used, including, e.g., tube and plunger type arrangements that can be plastic, paper, or other suitable material, rotating applicators, such as, e.g., described in U.S. patent application Ser. No. 11/703,919, to Gann, et al., titled "Self-Orienting Applicator," filed on Feb. 8, 2007, and/or compact type applicators.

The applicator can be constructed from any suitable material. Suitable materials include, for example, polyethylene, polypropylene, polybutylene, polystyrene, polyvinylchloride, polyacrylate, polymethacrylate, polyacrylnitril, polyacrylamide, polyamide, nylon, polyimide, polyester, polycarbonate, ethylene vinyl acetate, polyurethane, silicone, derivatives thereof, copolymers thereof, mixtures thereof, paper, paperboard, cardboard, any combinations thereof, or any suitable smooth plastic material. Examples of suitable materials are disclosed in, e.g., U.S. Pat. No. 5,346,468 issued to Campion, et al. on Sep. 13, 1994 and U.S. Pat. No. 5,558,631 issued to Campion, et al. on Sep. 24, 1996. Additives, such as, e.g., additives to alter or to enhance certain material properties, can also be included in the material. Suitable additives include, for example, mold release agents, colorants, slip agents, surface energy modifiers, pearlescent agents, and/or other suitable additives. In certain embodiments, the applicator can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the applicator can include one or more textured surfaces. Texture can be designed into or added to the applicator surface.

In certain embodiments, the applicator can be formed from a material that is adapted to allow a tampon having an improved aspect ratio to rotate relative to the barrel of the applicator when one or more intravaginal body pressures of a user act on the barrel. For example, the applicator can permit a tampon with an improved aspect ratio to twist within the barrel during and/or after insertion of the applicator into the user's body such that the tampon is properly oriented in the user's body. Because the applicator can be formed from a soft material, there can be less resistance to rotation of the tampon within the barrel due to the user's body pressure acting through the soft material of the applicator during and/or after insertion. The soft material can be any suitable material for facilitating rotation of a tampon having an improved aspect ratio relative to the barrel of the applicator, such as one or more plastics, such as, e.g., low and high density polyethylenes. In certain embodiments, the applicator can further comprise a grip portion, such as, e.g., a grip portion being adapted to provide a support for a user's fingers during use of the applicator.

A method of positioning a tampon having an improved aspect ratio in the vagina of a woman is also provided. In certain embodiments, the method includes positioning at least a portion of a tampon substantially between the cervix and the posterior wall of a vagina of a woman. The method can include providing a tampon having an improved aspect ratio and inserting the tampon into the vagina, such that one or more intravaginal body pressures of the woman position the tampon such that the width of the tampon is substantially aligned with the width of the vagina. In certain embodiments, the intravaginal body pressures of the woman can orient the tampon such that the width of the tampon is substantially aligned with the width of the vagina upon insertion and prior to loss of the self-sustaining form. In certain embodiments, the tampon can be positioned with the width of the tampon substantially aligned with the width of the vagina within about 30 minutes of insertion of the tampon into the vagina, such as, e.g., within about 25 minutes, within about 20 minutes, within about 15 minutes, within about 10 minutes, within about 5 minutes, and/or upon insertion of the tampon into the vagina.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon comprising a self-sustaining, fluid-expanding, compressed absorbent pledget comprising one or more absorbent materials that are cotton and/or rayon; the tampon having a width, a thickness, and a length, the width being greater than the thickness, a first cross-sectional shape proximate a tampon insertion end, a second cross-sectional shape proximate a tampon withdrawal end, and a third cross-sectional shape between the tampon insertion end and the tampon withdrawal end, wherein an aspect ratio of the width to the thickness of the third cross-sectional shape is from greater than about 1.4:1 to less than about 2:1, and wherein the third cross-sectional shape is different in shape versus at least one of the first cross-sectional shape and the second cross-sectional shape, wherein the third cross-sectional shape is oval.

2. A tampon comprising a self-sustaining, fluid-expanding, compressed absorbent pledget comprising one or more absorbent materials that are cotton and/or rayon; the tampon having a width, a thickness, and a length, the width being greater than the thickness, a first cross-sectional shape proximate a tampon insertion end, a second cross-sectional shape proximate a tampon withdrawal end, and a third cross-sectional shape between the tampon insertion end and the tampon withdrawal end, wherein an aspect ratio of the width to the thickness of the third cross-sectional shape is from greater than about 1.4:1 to less than about 2:1, and wherein the third cross-sectional shape is different in shape versus at least one of the first cross-sectional shape and the second cross-sectional shape, wherein the third cross-sectional shape is a prolate spheroid.

* * * * *